US012721758B2

(12) United States Patent
Sharma et al.

(10) Patent No.: US 12,721,758 B2
(45) Date of Patent: Sep. 1, 2026

(54) MEDICAL SYSTEMS, DEVICES, AND RELATED METHODS

(71) Applicant: Boston Scientific Medical Device Limited, Galway (IE)

(72) Inventors: Deepak Kumar Sharma, Muzaffarnagar (IN); Sharath Kumar G, Kanakapura (IN)

(73) Assignee: Boston Scientific Medical Device Limited, Galway (IE)

( * ) Notice: Subject to any disclaimer, the term of this patent is extended or adjusted under 35 U.S.C. 154(b) by 234 days.

(21) Appl. No.: 18/485,412

(22) Filed: Oct. 12, 2023

(65) Prior Publication Data

US 2024/0122771 A1 Apr. 18, 2024

Related U.S. Application Data

(60) Provisional application No. 63/379,796, filed on Oct. 17, 2022.

(51) Int. Cl.
*A61B 1/018* (2006.01)
*A61F 13/26* (2006.01)
(Continued)

(52) U.S. Cl.
CPC ............ *A61F 13/266* (2013.01); *A61B 1/018* (2013.01); *A61B 2017/00296* (2013.01); *A61B 2017/00584* (2013.01); *A61B 17/08* (2013.01); *A61B 17/083* (2013.01); *A61B 17/10* (2013.01); *A61B 17/11* (2013.01); *A61B 2017/1107* (2013.01);
(Continued)

(58) Field of Classification Search
CPC ........... A61B 2017/00296; A61B 2017/12018; A61B 17/08; A61B 17/083; A61B 17/10; A61B 17/11; A61B 2017/1107; A61B 17/1114; A61B 17/12; A61B 2017/12004;
(Continued)

(56) References Cited

U.S. PATENT DOCUMENTS 5,487,732 A * 1/1996 Jeffrey ................ A61M 5/3234
604/218
10,499,920 B2 * 12/2019 Hall .......................... A61F 2/07
(Continued)

FOREIGN PATENT DOCUMENTS

EP 2108315 B1 9/2017

OTHER PUBLICATIONS

International Search Report and Written Opinion issued in International Application No. PCT/IB2023/060309, issued Jan. 4, 2024 (11 pages).

*Primary Examiner* — Darwin P Erezo
*Assistant Examiner* — Mitchell Brian Hoag
(74) *Attorney, Agent, or Firm* — Bookoff McAndrews PLLC

(57) ABSTRACT

A medical device includes a handle including a main body and a movable body, a sheath element coupled to the handle, an actuation element disposed within the sheath element, an end cap configured to be coupled to a distal end of another medical device, and a patch positioned on the end cap and coupled to the actuation element. The patch includes a mesh and an expandable structure coupled to the mesh. The expandable structure is configured to be coupled to the actuation element, and the expandable structure is further configured to cause the mesh to retract and expand.

20 Claims, 10 Drawing Sheets

(51) Int. Cl.

| | |
|---|---|
| *A61B 17/00* | (2006.01) |
| *A61B 17/08* | (2006.01) |
| *A61B 17/10* | (2006.01) |
| *A61B 17/11* | (2006.01) |
| *A61B 17/12* | (2006.01) |
| *A61F 2/95* | (2013.01) |
| *A61F 2/954* | (2013.01) |
| *A61F 13/20* | (2006.01) |

(52) U.S. Cl.
CPC ........... *A61B 17/1114* (2013.01); *A61B 17/12* (2013.01); *A61B 2017/12004* (2013.01); *A61B 17/12009* (2013.01); *A61B 2017/12018* (2013.01); *A61F 2/95* (2013.01); *A61F 2/954* (2013.01); *A61F 2013/2014* (2013.01)

(58) Field of Classification Search
CPC ............ A61B 17/12009; A61B 17/005; A61B 2017/00584; A61F 2/95; A61F 2/954
See application file for complete search history.

(56) References Cited

U.S. PATENT DOCUMENTS

| | | | | | |
|---|---|---|---|---|---|
| 10,595,888 | B2 | 3/2020 | Hong et al. | | |
| 10,925,710 | B2 * | 2/2021 | Hall | A61F 2/06 | |
| 11,678,970 | B2 * | 6/2023 | Folan | A61F 2/064 | 623/1.2 |
| 2002/0032454 | A1 * | 3/2002 | Durgin | A61B 17/1227 | 606/151 |
| 2002/0062130 | A1 * | 5/2002 | Jugenheimer | A61B 17/1285 | 606/142 |
| 2002/0083641 | A1 * | 7/2002 | Leppard | C08J 5/18 | 47/29.4 |
| 2003/0229365 | A1 * | 12/2003 | Whayne | A61B 17/11 | 606/153 |
| 2005/0070758 | A1 * | 3/2005 | Wells | A61B 17/1285 | 600/104 |
| 2005/0080440 | A1 * | 4/2005 | Durgin | A61B 17/122 | 606/151 |
| 2005/0192604 | A1 * | 9/2005 | Carson | A61F 2/2493 | 606/153 |
| 2005/0256532 | A1 * | 11/2005 | Nayak | A61B 17/0057 | 606/151 |
| 2007/0282353 | A1 * | 12/2007 | Surti | A61B 17/1285 | 606/142 |
| 2007/0293875 | A1 * | 12/2007 | Soetikno | A61B 17/1227 | 606/142 |
| 2009/0138072 | A1 * | 5/2009 | Gendreau | A61B 50/30 | 623/1.2 |
| 2009/0264919 | A1 | 10/2009 | Sater et al. | | |
| 2010/0130993 | A1 * | 5/2010 | Paz | A61B 17/11 | 606/153 |
| 2011/0152888 | A1 * | 6/2011 | Ho | A61B 1/00087 | 606/151 |
| 2011/0190578 | A1 * | 8/2011 | Ho | A61B 1/00089 | 600/104 |
| 2012/0143141 | A1 * | 6/2012 | Verkaik | A61M 60/863 | 604/174 |
| 2013/0072943 | A1 * | 3/2013 | Parmar | A61B 34/20 | 606/130 |
| 2013/0123807 | A1 * | 5/2013 | Wells | A61B 17/083 | 606/142 |
| 2015/0201946 | A1 * | 7/2015 | Shepard | A61B 17/1227 | 606/142 |
| 2015/0305741 | A1 * | 10/2015 | Satake | A61B 17/1285 | 606/142 |
| 2018/0078745 | A1 * | 3/2018 | Gray | A61B 1/00101 | |
| 2018/0085122 | A1 * | 3/2018 | Ryan | A61B 17/1227 | |
| 2019/0231353 | A1 * | 8/2019 | Saenz Villalobos | A61B 17/122 | |
| 2020/0100791 | A1 * | 4/2020 | Tsuchiya | A61B 17/122 | |
| 2020/0397445 | A1 * | 12/2020 | Shikhman | A61B 17/1227 | |
| 2021/0045747 | A1 * | 2/2021 | Zhong | A61B 17/064 | |
| 2021/0059677 | A1 * | 3/2021 | Jin | A61B 17/122 | |
| 2022/0110652 | A1 * | 4/2022 | Gregan | A61B 1/0014 | |

* cited by examiner 200
212A
210
214
220
212D
212B
212C

P
122
118
119
129
116
D
120
128
116

MEDICAL SYSTEMS, DEVICES, AND RELATED METHODS

CROSS-REFERENCE TO RELATED APPLICATIONS

This application claims the benefit of priority under 35 U.S.C. § 119 from U.S. Provisional Application No. 63/379,796, filed Oct. 17, 2022, which is incorporated by reference herein in its entirety.

TECHNICAL FIELD

The disclosure relates generally to systems, devices, and methods for delivering patches. More specifically, aspects of the disclosure pertain to systems, devices, and/or methods for delivering patches, for example, for hemostasis, via medical devices, such as endoscopes.

BACKGROUND

Bleeding ulcers, for example, in a subject's gastrointestinal (GI) tract, are often difficult to manage and/or provide hemostasis. For example, common treatments for bleeding ulcers include injection therapies, thermal therapies, mechanical therapies, and hemostatic powders. Such therapies are often expensive and/or time-consuming. Furthermore, such therapies may not be able to treat a larger surface area, for example, a larger ulcer in the GI tract. Additionally, a common treatment for chronic ulcers is a gastric bypass. Such procedures may be more difficult, more time-consuming, more costly, and/or less effective/accurate than a minimally-invasive procedure to position a patch on one or more ulcers. Therefore, a need exists for systems, devices, and/or methods for positioning and/or deploying one or more hemostatic patches with one or more portions of a subject.

SUMMARY

This disclosure includes medical systems and devices comprising a biocompatible patch and methods of use thereof, e.g., methods of delivering a patch to a target site of a patient, for example, to help heal an ulcer and/or to perform hemostasis.

In one or more examples, a medical device may include a handle including a main body and a movable body, a sheath element coupled to the handle, an actuation element disposed within the sheath element, an end cap configured to be coupled to a distal end of another medical device, and a patch positioned on the end cap and coupled to the actuation element. The patch may include a mesh, and an expandable structure may be coupled to the mesh. The expandable structure may be configured to be coupled to the actuation element, and where the expandable structure may be further configured to cause the mesh to retract and expand.

Any of the medical devices described herein may include any of the following features. A release mechanism may be coupled to the expandable structure. The release mechanism may be further coupled to a pull wire radially disposed within the actuation element. The handle may include a portion configured to decouple the pull wire from the actuation element such that the pull wire moves independently of the actuation element. The release mechanism may include a ball and a yoke, where the ball may be coupled to a distal end of the pull wire, and where the ball may be configured to fit within a slot disposed in the yoke. The ball may be configured to be detached from the yoke to release the expandable structure from the actuation element. The expandable structure may include a star-shaped configuration. The star-shaped configuration may include at least four pointed segments. The expandable structure may include a shape memory material. The actuation element may be configured to move the patch from a first position to a second position. The patch may be positioned on the end cap when the patch is in the first position, and wherein the patch may be in a position distal to a distal end of the end cap when the patch is in the second position. The patch may be configured to remain in a retracted configuration when in the first position. The patch may be configured to expand into an expanded configuration when in the second position. The patch further may include a central opening. The patch may be at least partially transparent.

According to another example, a method of delivering a biocompatible patch to a target site of a patient may include introducing a medical system into a lumen of a patient, the medical system may include a scope, a medical device, which may include a handle including a movable body and a main body, an end cap coupled to a distal end of the scope, a sheath element connecting the handle to the end cap, an actuation element disposed within the sheath element, and a patch including a biocompatible mesh and an expandable structure. A release mechanism may be coupled to each of the expandable structure and the actuation element The method may also include positioning a distal end of the scope proximate the treatment site, moving the patch from a first position to a second position by moving the movable body of the handle distally with respect to the medical device, and releasing the patch from the medical device, where releasing the patch from the medical device may include uncoupling at least a portion of the release mechanism from the expandable structure.

Any of the methods described herein may include any of the following features. The medical device further may include a pull wire disposed within, and coupled to, the actuation element, where the pull wire may be further coupled to the release mechanism, where the handle further may include a decoupling portion configured to decouple the pull wire from the actuation element such that the pull wire moves independently of the actuation element, and where releasing the patch from the medical device may include engaging the release mechanism by decoupling the pull wire from the actuation element, and separating the pull wire from the release mechanism. A distal end of the scope may include a visualization device, and the method further may include visualizing the second position relative to the treatment site with the visualization device, moving the patch from the second position back to the first position, and repositioning the distal end of the scope proximate the target site.

According to another example, a medical device may include a handle disposed at a proximal end of the medical device, the handle may include a main body, a movable body, and a decoupling mechanism. The medical device may also include a sheath element, an actuation element disposed within the sheath element and coupled to the decoupling mechanism, a pull wire disposed within the actuation element and coupled to the decoupling mechanism, an end cap configured to be coupled to a distal end of another medical device, and a patch positioned on the end cap. The patch may include a biocompatible mesh, an expandable structure coupled to the biocompatible mesh, and a release mechanism coupled to each of the expandable structure and the pull wire. The expandable structure may be configured to cause the patch to expand.

Any of the medical devices described herein may include any of the following features. The release mechanism may include a yoke portion and a ball portion configured to fit within a slot of the yoke portion. The ball portion may extend from the pull wire.

Any of the examples described herein may have any of these features in any combination.

BRIEF DESCRIPTION OF THE DRAWINGS

The accompanying drawings, which are incorporated in and constitute a part of this specification, illustrate examples of this disclosure and together with the description, serve to explain the principles of the disclosure.

DETAILED DESCRIPTION

Reference will now be made in detail to aspects of this disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., patient). By contrast, the term "proximal" refers to a portion closest to the user when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Figure 1A:
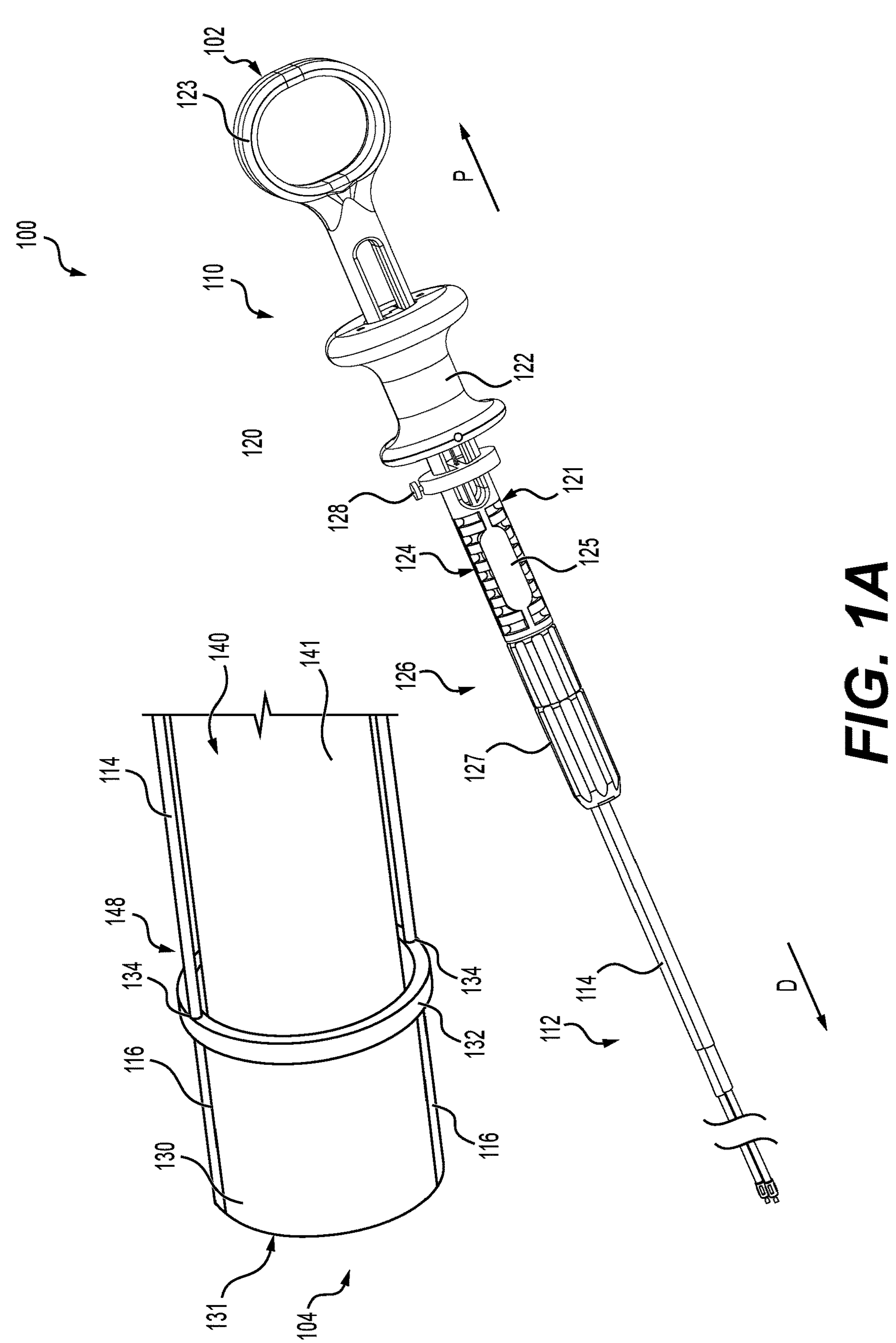
FIG. 1A depicts a perspective view of an exemplary medical system, including an exemplary medical device and an endoscope, according to some embodiments.

FIG. 1A depicts a perspective view of a medical system 100, for example, including a medical device 110 and an endoscope 140, which may be coupled to a distal end of medical device 110. As discussed in detail herein, medical device 110 may include or otherwise be coupled to a patch delivery system, for example, to position and/or deliver a patch 200 (shown in FIGS. 1B and 2B). The patch delivery system may be disposed on a distal end of endoscope 140, such that patch 200 may be positioned and/or delivered to one or more portions of tissue within a subject, which may help perform hemostasis within the subject. Moreover, medical device 110 may be coupled to one or more portions of an endoscope 140, for example, a distal portion 148 of endoscope 140, in order to deliver one or more portions of medical device 110 to a treatment site.

Endoscope 140 may include a flexible tubular shaft 141. The flexibility of shaft 141 may be sufficient to allow shaft 141 to bend, to facilitate navigation of shaft 141 through a subject's tortuous anatomical passages. Shaft 141 may terminate at a distal portion 148, and may be any suitable length. Endoscope 140 also may include one or more lumens extending therethrough, and one or more openings in communication with the one or more lumens (such as an opening, for example working channel 143, at a distal face 149 of endoscope 140, as shown in FIG. 2A).

Although the treatment site is discussed herein as being in the subject's GI tract, this disclosure is not so limited, as the treatment site may be any internal lumen, organ, cavity, or other tissue within the subject. Additionally, although endoscopes are referenced herein, it will be appreciated that the disclosure encompasses any medical devices having a working channel extending from a proximal end to a distal end, such as ureteroscopes, duodenoscopes, gastroscopes, endoscopic ultrasonography ("EUS") scopes, colonoscopes, bronchoscopes, laparoscopes, arthroscopes, cystoscopes, aspiration scopes, sheaths, or catheters.

Figure 2A:
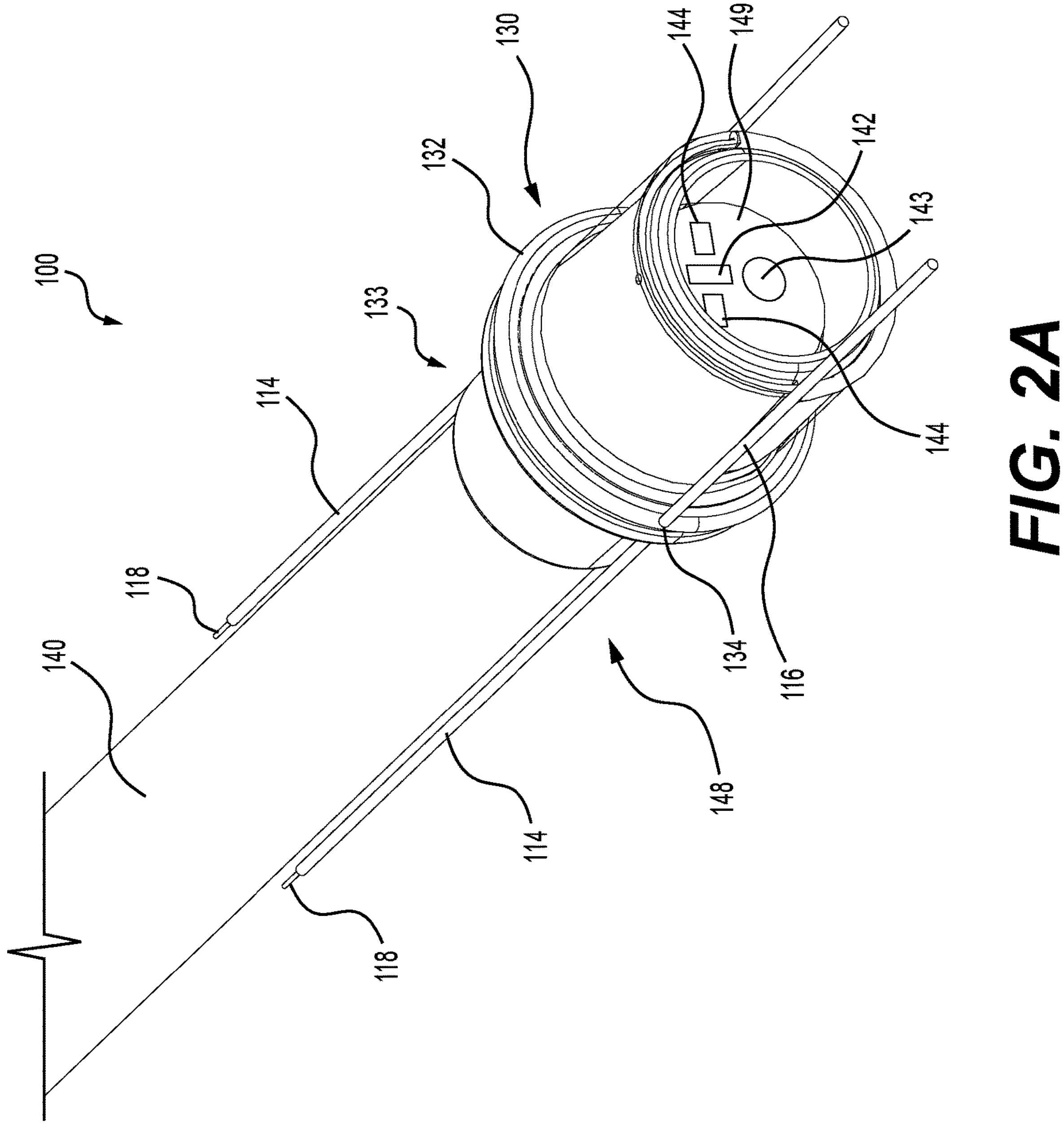
FIG. 2A depicts a perspective view of a distal portion of an exemplary medical system, according to some embodiments.

Still referring to FIG. 2A, endoscope 140 may have a diameter of approximately 9 mm to approximately 15 mm, for example, approximately 10.5 mm to approximately 12 mm. As mentioned, endoscope 140 may include one or more internal lumens, for example, working channel 143 with a diameter of approximately 2 mm to approximately 4 mm, for example, approximately 2.8 mm. Additionally, a distal face 149 of endoscope 140, may include one or more illumination device(s) 144 (e.g., one or more LEDs, optical fibers, and/or other illuminators) and/or one or more visualization device(s) 142 (e.g., one or more cameras, one or more image sensors, endoscopic viewing elements, optical assemblies including one or more image sensors and one or more lenses, etc.).

Referring back to FIG. 1A, medical device 110 may include a handle assembly 120 and an end cap 130. End cap 130 may be coupled to distal portion 148 of endoscope 140 at a distal end 104 of medical system 100. For example, end cap 130 of medical device 110 may be coupled to distal portion 148 (e.g., a distal end) of endoscope 140, and may have a size and/or shape configured to be coupled to (e.g., radially surround) distal portion 148 of endoscope 140. End cap 130 may be coupled to endoscope 140 before insertion of endoscope 140 into the subject, such that end cap 130 and distal portion 148 of endoscope 140 may be delivered to the treatment site. Then, the user may manipulate one or more portions of handle assembly 120 to control (e.g., extend or retract) one or more portions of end cap 130. Furthermore, although not shown, endoscope 140 may include one or more proximal controls (dials, levers, buttons, etc.), for example, to extend or retract, deflect, or otherwise control the position of distal portion 148 of endoscope 140, and thus control the position of end cap 130.

In some embodiments, handle assembly 120 may be located at a proximal end 102 of medical device 110, and may include a main body 121 and a movable body 122. Main body 121 may be generally cylindrical and may include a ring portion 123 at a proximalmost end of main body 121. Ring portion 123 may be configured to receive one or more of a user's fingers to facilitate holding handle assembly 120. Main body 121 may include one or more ridged portions 124, for example, configured to facilitate gripping main body 121. Main body 121 may also include a slot 125, for example, extending longitudinally through a portion of main body 121. Slot 125 may be configured to movably receive a portion of movable body 122. A distal end portion 126 of main body 121 may include a coupler portion 127, which may be cylindrical and may help couple an actuator assembly 112 to main body 121. Movable body 122 may be cylindrical, may be hour-glass shaped, and may be configured to receive one or more fingers to facilitate movement of movable body 122 relative to main body 121.

Actuator assembly 112 may be configured to move proximally and distally through coupler portion 127. Actuator assembly 112 may include a sheath element, for example, outer coil 114, and an actuation element, for example inner coil 116, movably disposed within outer coil 114. Inner coil 116 may be configured to move proximally and distally, within outer coil 114, with respect to medical device 110, and may be coupled to a decoupling mechanism 128. Decoupling mechanism 128 may be disposed on main body 121, for example, distal to movable body 122.

In some embodiments, a pull wire 118 may be disposed within, and detachably coupled to, inner coil 116, and may be configured to move simultaneously with inner coil 116. Pull wire 118 may also be coupled to decoupling mechanism 128, and decoupling mechanism 128 may be manipulated in order to decouple pull wire 118 from inner coil 116 to allow pull wire 118 to move independently of inner coil 116, as will be discussed in greater detail, below.

Although not shown, a lumen may extend through main body 121 and coupler portion 127, for example, to allow actuator assembly 112 to be positioned within main body 121 and move within main body 121. A proximal end of actuator assembly 112 may be coupled to movable body 122. In these aspects, proximal and/or distal movement of movable body 122 longitudinally relative to main body 121 may move actuator assembly 112 proximally and/or distally, respectively. For example, movement of movable body 122 distally may cause inner coil 116 to simultaneously move distally.

Figure 1B:
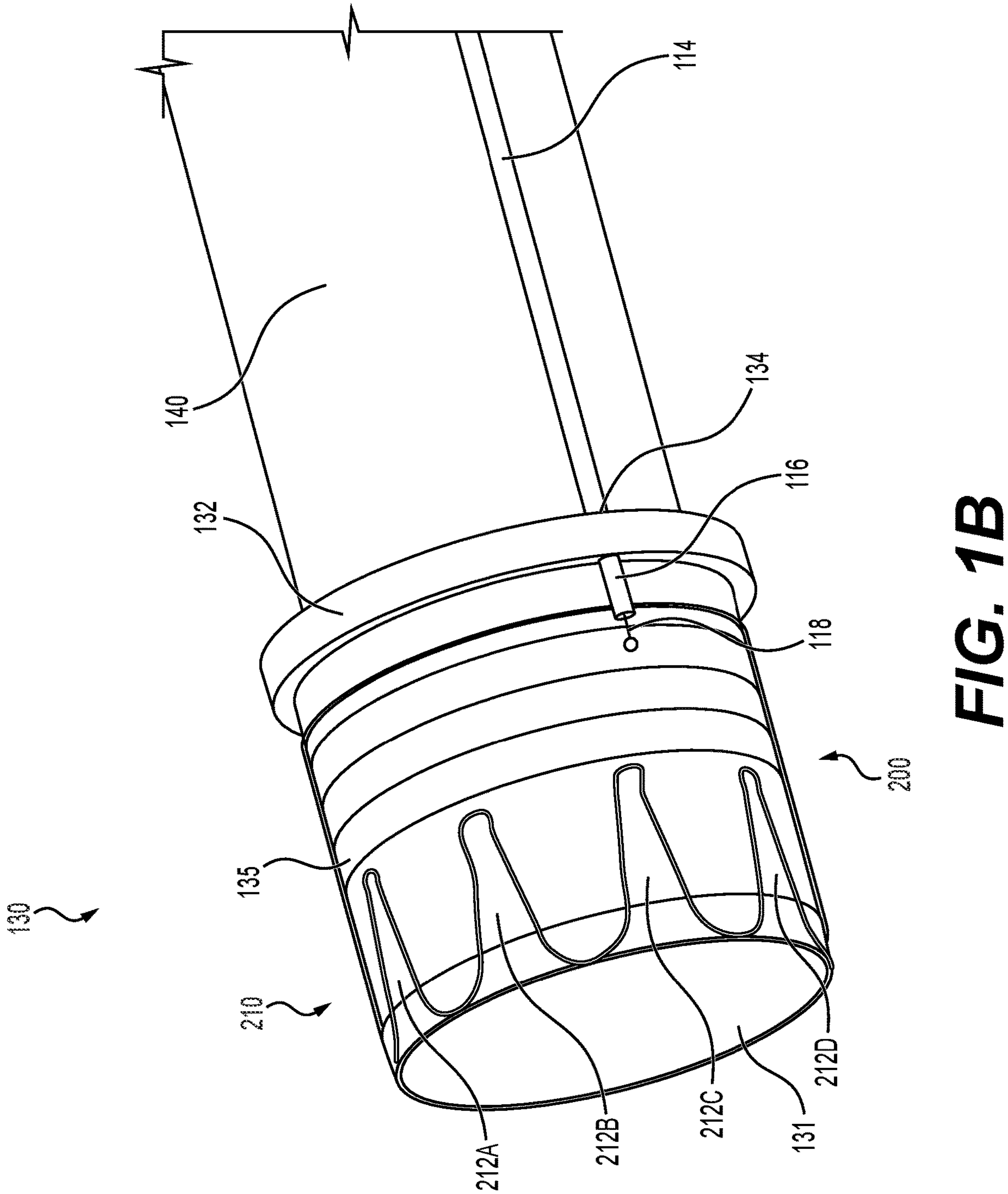
FIG. 1B depicts a perspective view of a distal portion of the exemplary medical system of FIG. 1A, according to some embodiments.
Figure 2B:
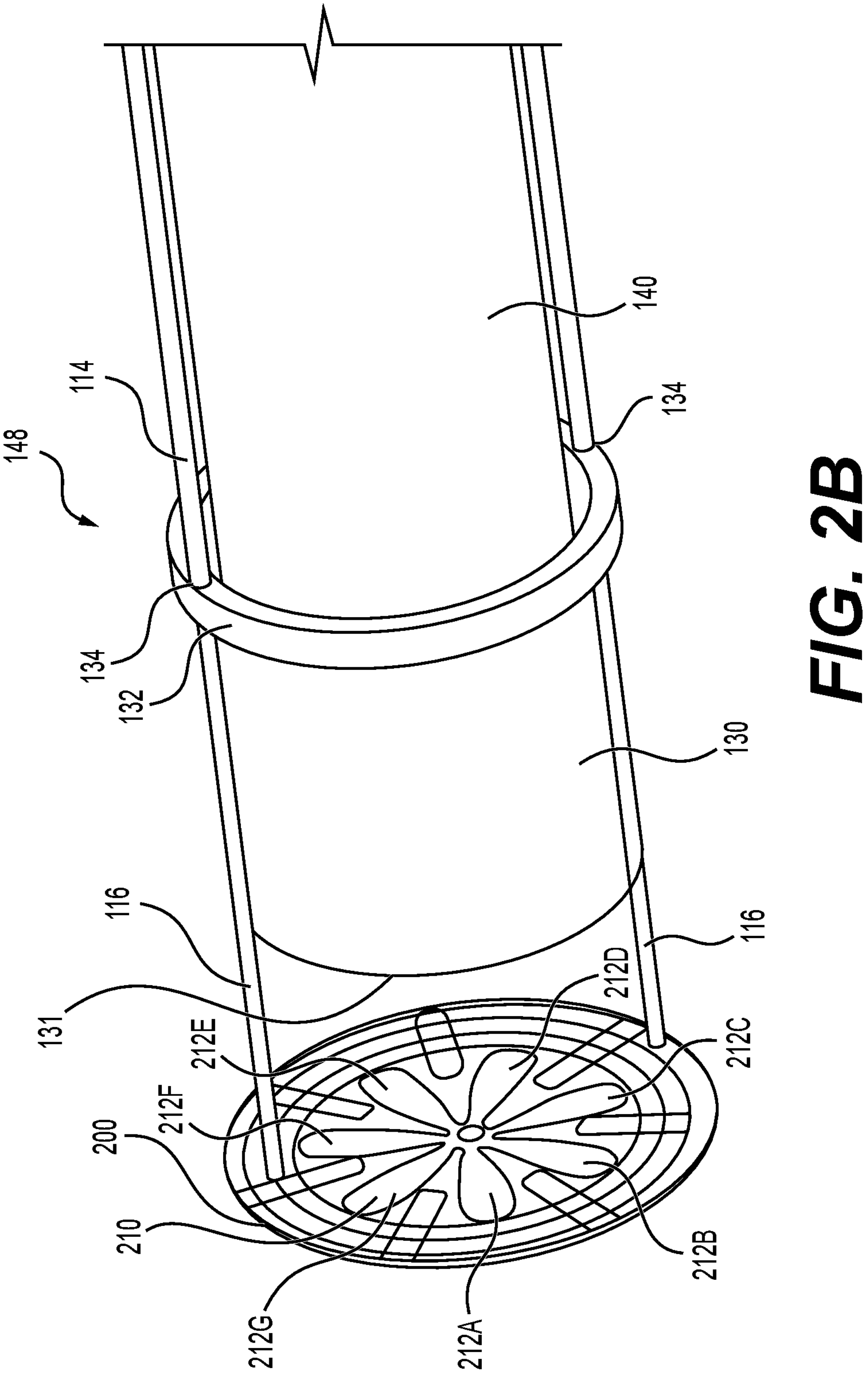
FIG. 2B depicts a perspective view of the distal portion of the exemplary medical system of FIG. 2A, according to some embodiments.
Figure 8:
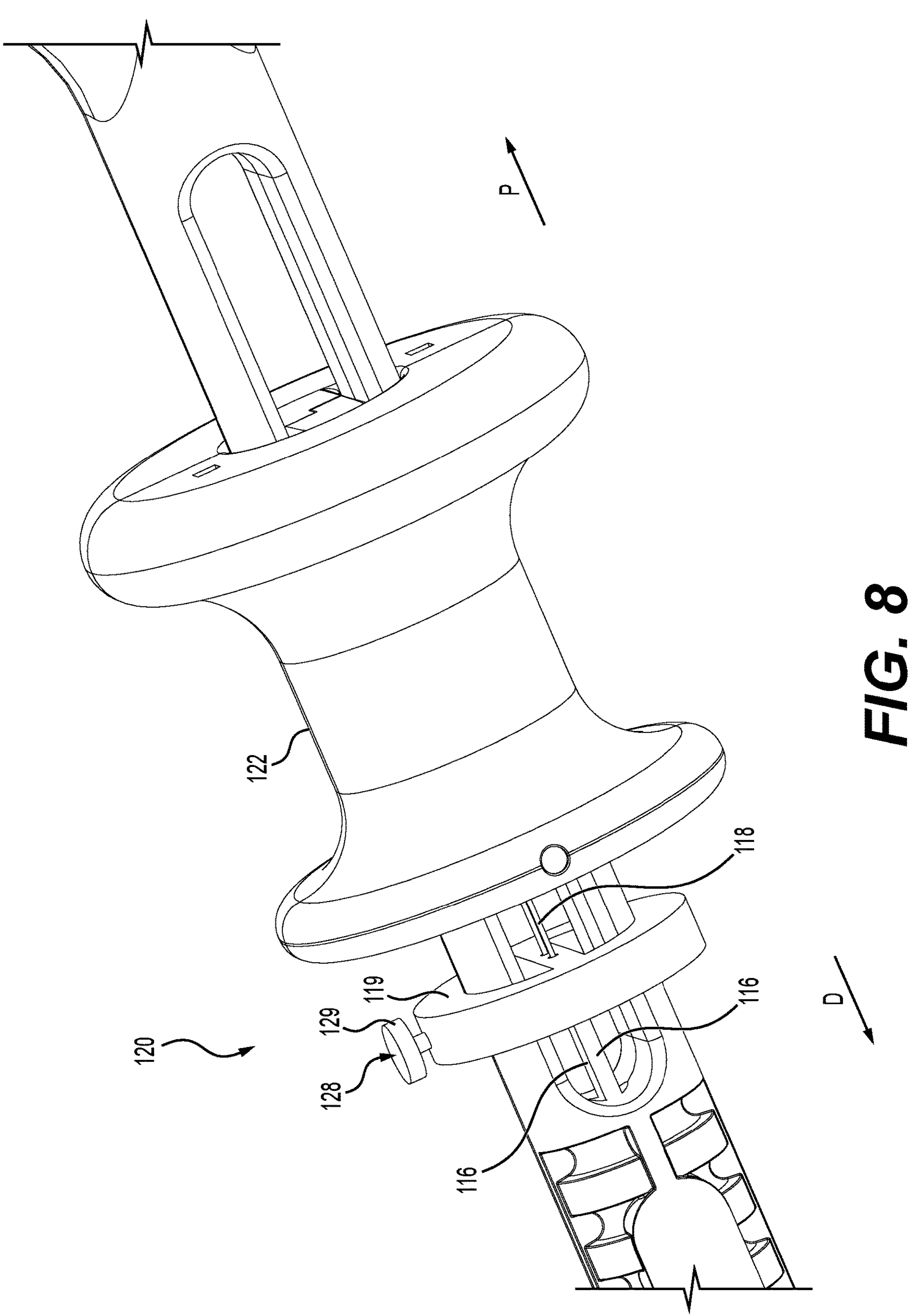
FIG. 8 depicts a perspective view of a portion of a handle for manipulating the medical device, according to some embodiments.

FIGS. 1B, 2A, and 2B illustrate various aspects of end cap 130, endoscope 140, and patch 200. It is noted, however, that patch 200 is omitted in FIG. 2A in order to show aspects of endoscope 140. As shown in FIG. 2B, in some embodiments, patch 200 may be releasably coupled to a distal end 131 of end cap 130. As discussed below, patch 200 may be releasably connected to inner coil 116 via a release mechanism (FIG. 8). The release mechanism may be secured to an expandable structure 210 within patch 200. In some examples, advancing movable body 122 proximally relative to main body 121 may be configured to transition patch 200 from a first position, e.g., adjacent to distal end 131, for example as shown in FIGS. 1A and 1B, to a second position, e.g., a location distal to distal end 131 of end cap 130.

In some embodiments, end cap 130 may be coupled to distal portion 148 of endoscope 140, for example, via a friction fit, an adhesive, a press fit, a crimping, or any other appropriate coupling mechanism. Additionally, end cap 130 may receive portions of one or more of sheath element(s), for example outer coil 114, and actuation element(s), for example inner coil 116.

In some embodiments, end cap 130 may include an end cap ring 132. For example, end cap ring 132 may extend radially outward from end cap 130, for example, between a proximal portion 133 of end cap 130 and a distal end 131 of end cap 130. Additionally, one or more portions of end cap ring 132 may include a radiopaque material (e.g., one or more markers, one or more gradients, etc.), or otherwise help the user to visualize end cap ring 132 or other portions of end cap 130. In some aspects, outer coil 114 may be coupled (e.g., fixedly coupled) to end cap 130, for example, to end cap ring 132 (e.g., via a friction fit, an adhesive, a press fit, a crimping, or any other appropriate coupling mechanism. In some embodiments, as shown in FIGS. 2A and 2B, distal ends (not shown) of outer coil(s) 114 may be coupled to end cap ring 132 within a respective through-hole 134 extending through end cap ring 132. Inner coil(s) 116 may extend through through-hole(s) 134, as inner coil(s) extend through outer coil(s) 114.

Figure 3:
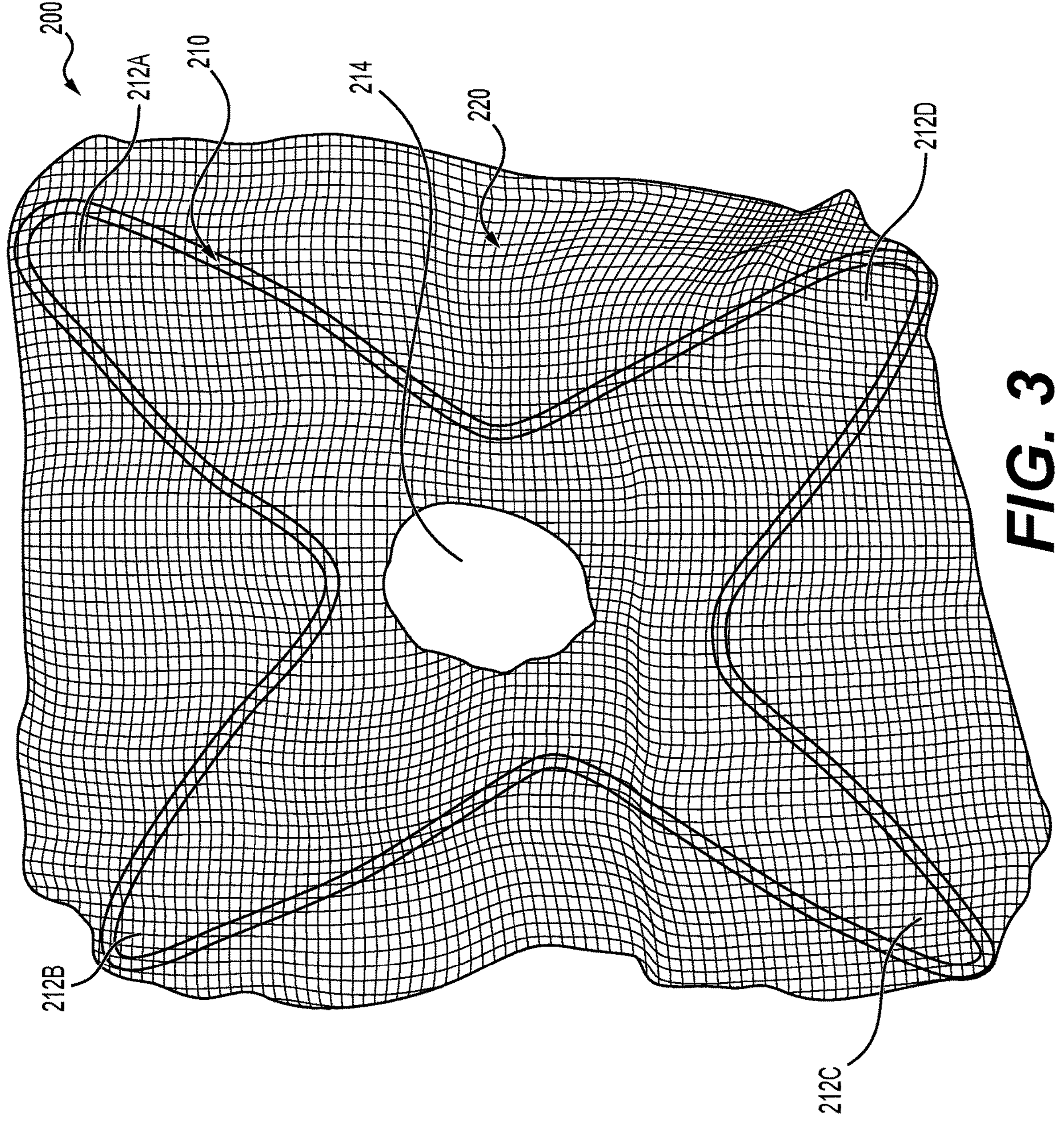
FIG. 3 depicts a top view of an exemplary patch, according to some embodiments.

FIG. 3 illustrates a top view of patch 200 in an expanded configuration, described above. Patch 200 may be a biodegradable and/or biocompatible patch of any suitable shape and any suitable dimension, e.g. based on the nature of the target tissue site. Patch 200 may be flexible and may have any shape such as, e.g., approximately square, approximately rectangular, rounded square, rounded rectangle, ovate, circular, among other possible shapes. In some embodiments, patch 200 may be at least partially transparent.

In some examples, the thickness of the patch may be on the order of millimeters, e.g., ranging from approximately 0.1 mm to approximately 5.0 mm or, more specifically, from approximately 0.7 mm to approximately 2.0 mm. Patch 200 may be sufficiently sized to cover the target tissue with a margin for resection. Thus, patch 200 can come in many sizes to accomplish such a task. In some aspects, patch 200 may be approximately 50 mm by 50 mm (i.e., approximately 2 inches by 2 inches).

Patch 200 may be of any suitable color, including clear, and may be formed of any suitable material, e.g., nettings, meshes, cloths, gelatins, or polysaccharides (chitosan, cellulose, starch, alginates, etc.) that may be further modified with synthetic biocompatible materials (pHEMA, PGA, PLA, PCA, PEG, etc.). In some aspects, patch 200 may be formed of a bioadhesive material, for example, such as chitosan, modified chitosan, cellulose, pHEMA, PVA, PEG, or composites of one or more of these polymers. Additionally, for example, patch 200 may be comprised of polypropylene, polyester, Polytetrafluoroethylene (PTFE), expanded Polytetrafluoroethylene (ePTFE), and/or silicone.

In some embodiments, patch 200 may be adhered to the target tissue using materials or fluids commonly known in the art, such as, for example, fibrin glue, hydrogel, and/or cyanoacrylate. Alternatively or additionally, patch 200 may be comprised of and/or dosed with agents to prevent the shedding of cells from the target tissue or to treat the target site. In some aspects, patch 200 may include a treatment agent, for example, an antibiotic and/or hemostatic agent. Moreover, after patch 200 is delivered to the treatment site, the user may spray, apply, or otherwise deliver one or more hemostatic agents (e.g., one or more hemostatic powders), for example, through working channel 143 of endoscope 140 or another medical device. Additionally, patch 200 may be adhered to tissue within the treatment site, for example at step 714, using materials commonly known in the art, such as, for example, fibrin glue, hydrogel, and/or cyanoacrylate.

Still referring to FIG. 3, patch 200 may include expandable structure 210 coupled to a mesh 220. Expandable structure 210 may be coupled to mesh 220 by an adhesive, or by any other suitable fixation mechanisms. For example, in some embodiments, expandable structure 210 may be interwoven with mesh 220. Alternatively, in some embodiments, expandable structure 210 may be tied to mesh 220 using a string, or may be fixed to mesh 220 using a UV curing technique. In some embodiments, expandable structure 210 may include at least one narrowed or pointed segment, for example, pointed segments 212A-D. In some embodiments, expandable structure 210 may be formed in the shape of a four-pointed star, and include at least four pointed segments 212A-D. However, expandable structure 210 may be formed in any shape, and/or and may include any number of pointed segments, for example, two, three, five, six, etc., for example as shown in FIG. 2B, where expandable structure 210 includes seven pointed segments 212A-G.

Expandable structure 210 may provide rigidity to mesh 220, and may be transitioned from a retracted state, for example as shown in FIGS. 1A and 1B, where a distal end of inner coil 116 is extended only as far as distal end 131 of end cap 130, to a deployed or expanded state (FIGS. 2B and 3). In the retracted state, expandable structure 210 may be configured to be abut or otherwise be positioned adjacent to distal end 131 of end cap 130. For example, as shown in FIG. 1B, expandable structure 210 may be positioned over end cap 130, and pointed segments 212A-D may be in a bent, or retracted, position over a sidewall 135 of end cap 130, thereby helping to ensure that patch 200 remains flush with end cap 130 prior to delivery of patch 200 to the treatment site. However, when the patch is delivered to the treatment site, the expandable structure 210 may be transitioned from the retracted state (FIGS. 1A and 1B) to an expanded state (FIG. 2B). In the expanded state, expandable structure 210 may open radially such that patch 200 may lay flat against a treatment site. By maintaining expandable structure 210 in the retracted state against end cap 130, patch 200 may have a larger size than other mesh patches used to treat ulcers, since patch 200 does not need to travel though working channel 143 of endoscope 140. Accordingly, larger treatment sites may be treated using patch 200. By being coupled to end cap 130 instead of being delivered to a treatment site through working channel 143 of endoscope 140, patch 200 there is no risk that patch 200 will become stuck or otherwise impair working channel 143. In some embodiments, expandable structure 210 may be made from a shape memory alloy or material, for example Nitinol, which may help the structure to expand from the retracted state to the expanded state.

In some embodiments, patch 200 may additionally include a central opening 214 extending through a central portion of mesh 220. Central opening 214 may include a diameter substantially equal to that of visualization device 142, disposed on distal face 149 of endoscope 140, and may be positioned over visualization device 142 such that visualization device 142 is not obstructed by patch mesh 220.

Figure 4:
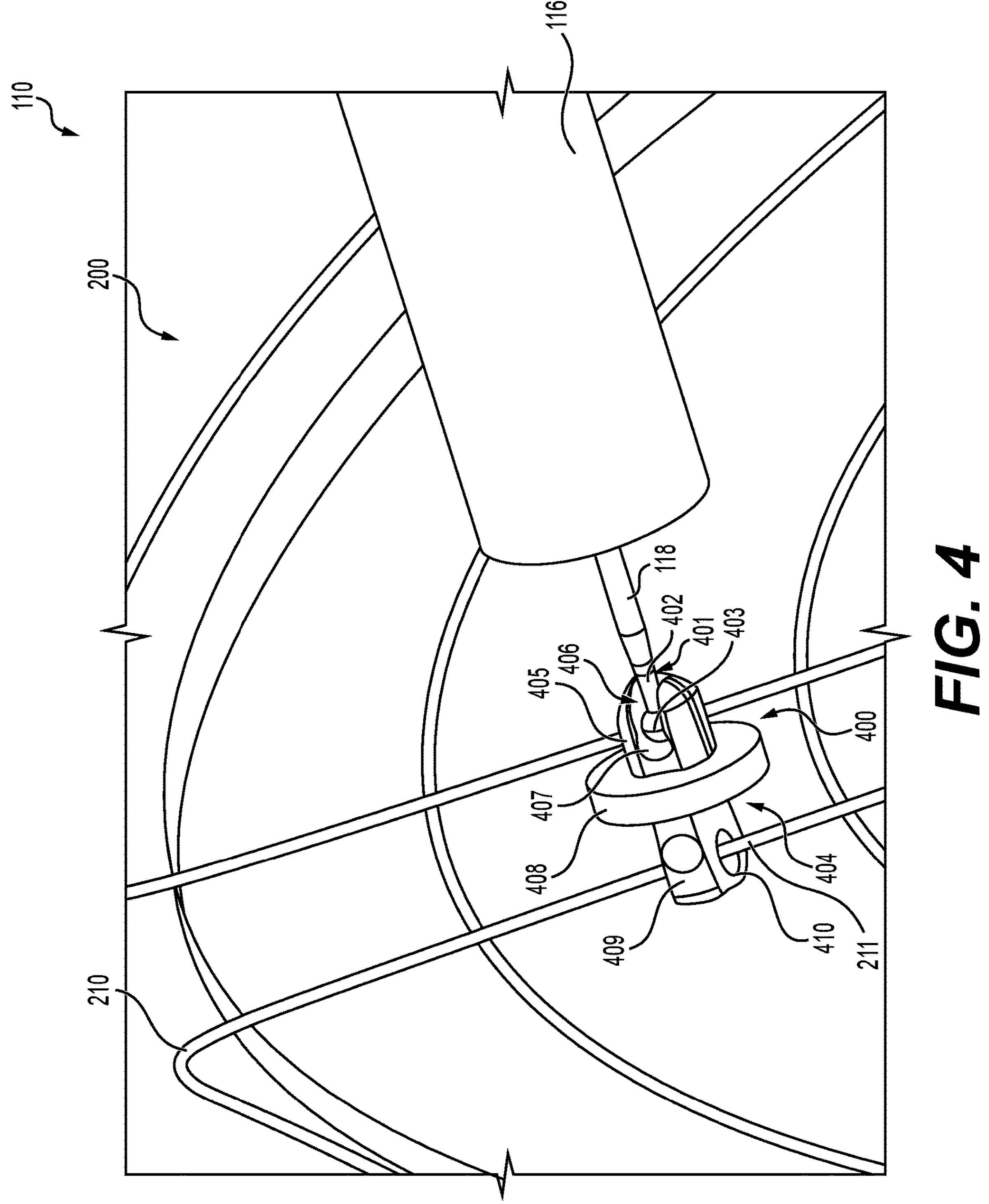
FIG. 4 depicts a perspective view of an exemplary release mechanism of a medical device, according to some embodiments.
Figure 5:
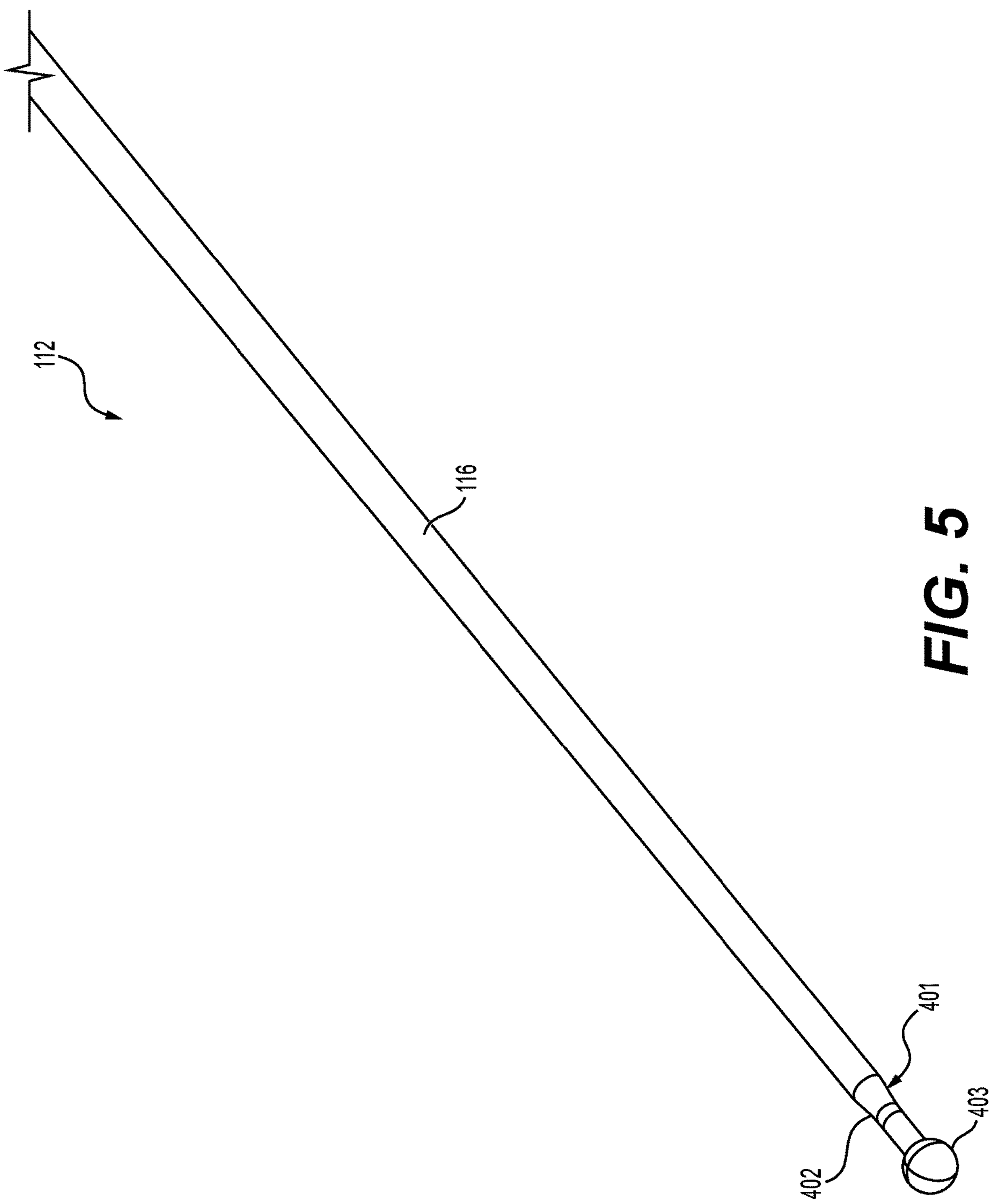
FIG. 5 depicts a perspective view of a ball portion of the exemplary release mechanism of FIG. 4, according to some embodiments.
Figure 6:
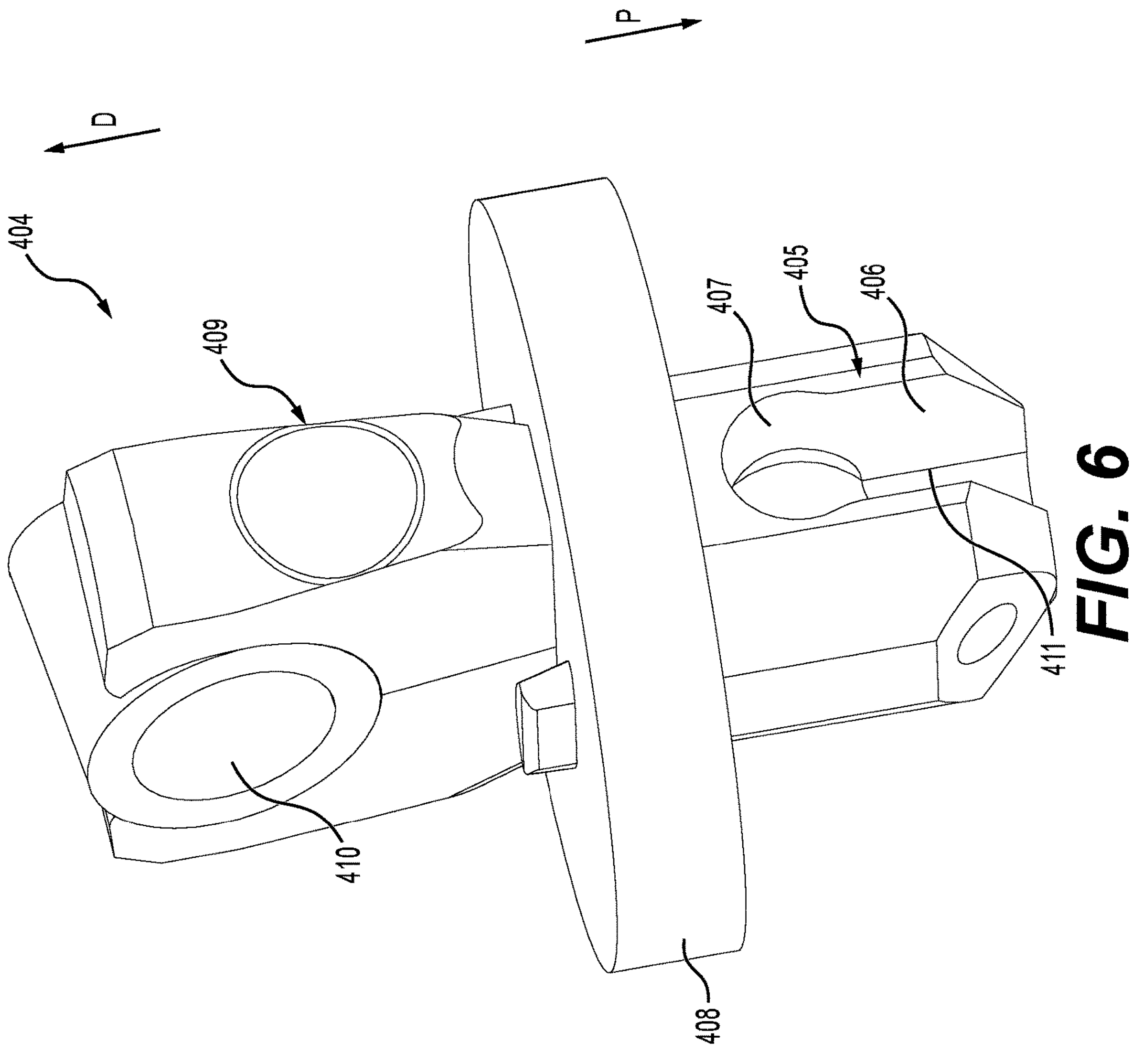
FIG. 6 depicts a perspective view of a yoke portion of the exemplary release mechanism of FIG. 4, according to some embodiments.

As shown in FIGS. 4-6, medical device 110 may additionally include a release mechanism 400, for example, configured to releasably couple patch 200 to medical device 110. FIG. 4 depicts a view of release mechanism 400 in a coupled configuration, where a ball portion 401, shown in detail in FIG. 5, is disposed within a yoke portion 404, shown in detail in FIG. 6.

In some embodiments, release mechanism 400 may help to couple patch 200 to end cap 130 while expandable structure 210 is in the retracted position. Release mechanism 400 may also help to facilitate the release of patch 200 from end cap 130 when expandable structure 210 is in the extended position, for example, when patch 200 is extended distally from end cap 130 (FIG. 2B), and is being delivered to a treatment site.

In some embodiments, release mechanism 400 may include a ball portion 401 extending from pull wire 118. A distal end of ball portion 401 may include a ball 403. Pull wire 118 may be movably positioned within inner coil 116, and may extend to handle assembly 120 (FIG. 1A). Release mechanism 400 may also include a yoke portion 404, which may be configured to be coupled to expandable structure 210 of patch 200. Yoke portion 404 may be coupled to expandable structure 210 via an opening 410 disposed in a distal portion 409 of yoke portion 404. For example, distal portion 409 may surround a portion 211 of expandable structure 210. In some embodiments, a diameter of opening 410 may be larger than a diameter of the portion 211 of expandable structure 210, which may allow release mechanism 400 to be movable, or slidable, along expandable structure 210 when expandable structure 210 transitions from the retracted state to the expanded state.

Yoke portion 404 may additionally include a slot 406, for example, in a proximal portion 405 of yoke portion 404. Yoke portion 404 may be configured to receive ball 403 of ball portion 401. Slot 406 may additionally include a substantially circular opening 407 at a distal end of slot 406. Opening 407 may have a diameter larger than a diameter of ball 403, such that ball 403 may be inserted into slot 406 via opening 407, but ball 403 then may be secured within an elongated portion 411 of slot 406. Elongated portion 411 may have a width approximately equal to the diameter of ball 403. Accordingly, ball 403 may fit snugly within elongated portion 411 of slot 406 prior to release, for example, such that one or more portions of ball 403 abuts portions of elongated portion 411. In some embodiments, ball portion 401 may additionally include a tapered portion 402 extending from pull wire 118 to ball 403. An angle of tapered portion 402 may facilitate insertion of ball portion 401 into opening 407, as a width of tapered portion 402 may be less than the width of elongated portion 411.

Additionally, yoke portion 404 may additionally include a central portion 408, disposed between proximal portion 405 and distal portion 409. Each of proximal portion 405 and distal portion 409 may be coupled to central portion 408. In some embodiments, central portion 408 may be cylindrical or circular; however, central portion 408 may be formed in any suitable shape.

As will be discussed in greater detail below, for example with respect to FIGS. 7 and 8, in some embodiments, ball portion 401 may be uncoupled, or detached from, from yoke portion 404 in order to uncouple patch 200 from end cap 130. For example, ball portion 401 may be entirely removed from yoke portion 404. Or, in some embodiments, ball portion 401 may be configured to break at tapered portion 402, thereby separating ball portion 401 from yoke portion 404.

Figure 7:
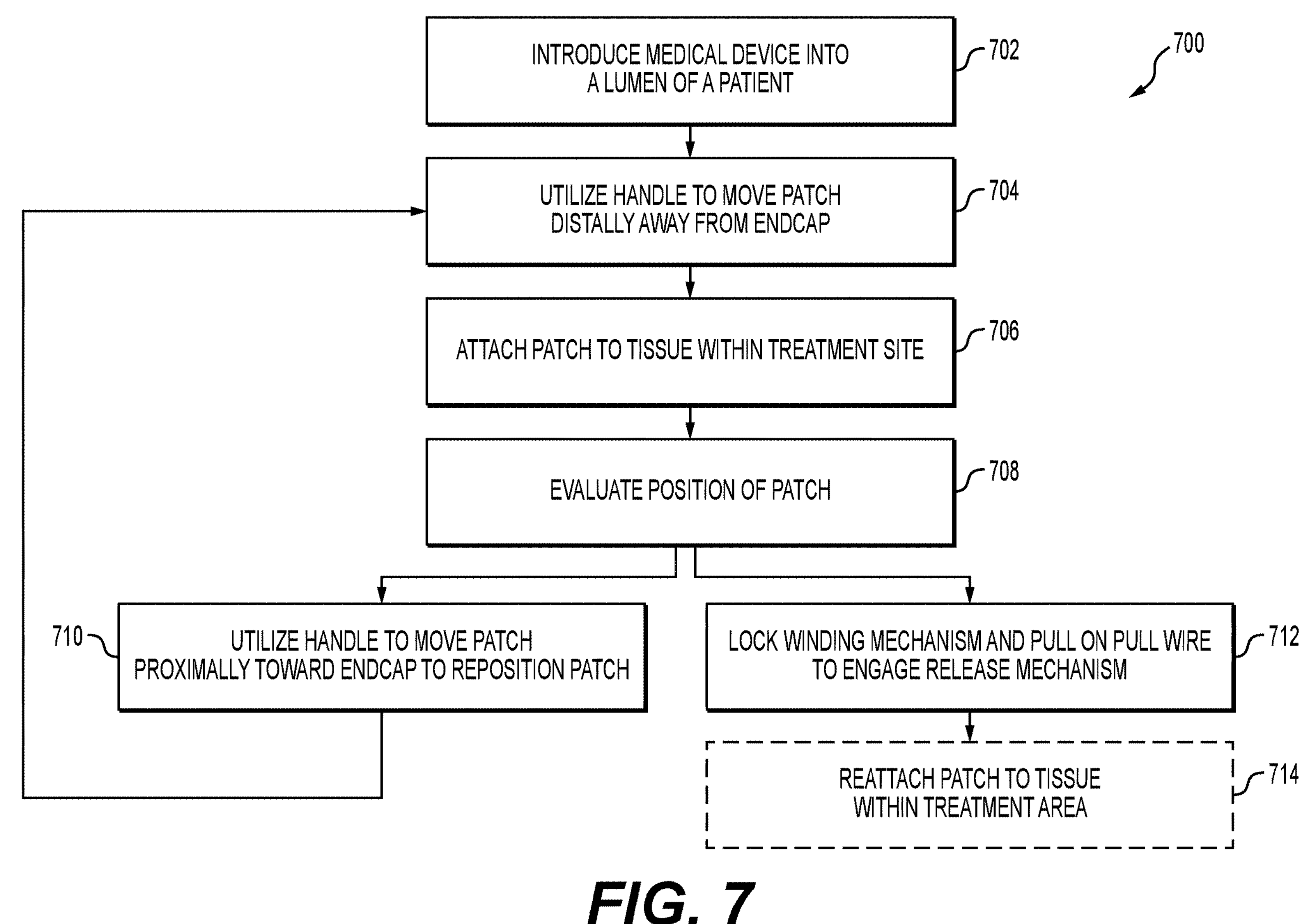
FIG. 7 is a block diagram depicting an exemplary method of delivering a biocompatible patch using an exemplary medical device, according to some embodiments.

As shown in the flow chart depicted in FIG. 7, in some embodiments, patch 200 may be positioned and repositioned before being deployed to the treatment site according to a method 700. For example, as shown in FIG. 8, inner coil 116 may be connected to decoupling mechanism 128, which may include, for example a spool 119, including a knob 129. Medical system 100 may be utilized to deliver and position end cap 130 at a treatment site by introducing medical device 110 into a lumen of a patient, for example at step 702. Once medical device 110 is introduced into the lumen, a user may utilize movable body 122 of handle assembly 120 to move patch 200, for example at step 704, by pushing movable body 122 in the distal direction. As inner coil 116 moves distally, patch 200 may be moved distally away from end cap 130 toward the treatment site, thereby transitioning expandable structure 210 from the retracted position to the expanded position. Once patch 200 is moved away from end cap 130, the user may attach patch 200 to tissue within the treatment site, for example at step 706. Once patch 200 is attached to tissue within the treatment site, the user may evaluate the position of patch 200, for example at step 708, as visualization device 142 on endoscope 140 may be unobstructed. If the user wishes to reposition patch 200 once its position has been determined, for example at step 710, movable body 122 of handle assembly 120 may be adjusted in the proximal direction to move patch 200 proximally back toward end cap 130. Alternatively, in some embodiments, patch 200 may be repositioned by adjusting an articulation section (not shown) of endoscope 140 to deflect distal portion 148 of endoscope 140 in proximal, distal, up, down, left, and/or right directions.

Once patch 200 has been positioned in a desired area over the treatment site, decoupling mechanism 128 may be manipulated, for example rotated via knob 129 (shown in FIG. 8) to transition decoupling mechanism 128 from a first configuration (FIGS. 1A and 1B) to a second configuration (FIG. 8). In the first configuration, pull wire 118 and inner coil 116 may be configured to move together, whereas in the second configuration, decoupling mechanism 128 may be configured to lock, or secure the position of, inner coil 116 relative to movable body 122. Accordingly, at step 712, for example, decoupling mechanism may be engaged such that it is manipulated into the second configuration, where the position of pull wire 118 may be adjusted independently of inner coil 116. For example, upon transitioning decoupling mechanism 128 into the second configuration, the user may pull on an end of pull wire 118, which may move independently of inner coil 116 when decoupling mechanism 128 is in the second configuration. As described above, ball portion 401 of release mechanism 400 may be coupled to pull wire 118. Accordingly, when pull wire 118 is pulled proximally with respect to medical device 110 with enough force, slot 406 of yoke portion 404, and/or a proximal face of central portion 408 of yoke portion 404, may interface with a distal end of inner coil 116, and ball portion 401 of release mechanism 400 may break free from yoke portion 404, thereby releasing, or deploying, patch 200 onto the treatment site. Once released, pointed segments 212A-G, as shown in FIG. 2B, may expand, thereby causing patch 200 to lay flush against the treatment site.

After patch 200 has been deployed to the treatment site, patch 200 may optionally be re-adhered to tissue within the treatment site, for example at step 714, using materials commonly known in the art, such as, for example, fibrin glue, hydrogel, and/or cyanoacrylate. Alternatively or additionally, after patch 200 is delivered to the treatment site, the user may spray, apply, or otherwise deliver one or more hemostatic agents (e.g., one or more hemostatic powders), for example, through working channel 143 of endoscope 140 or another medical device.

Additionally, in some embodiments, patch 200 may be positioned relative to the treatment site using one or more auxiliary medical devices, and/or the user may inspect the position of patch 200 at the treatment site, for example, via one or more visualization devices 142 on endoscope 140. Once patch 200 has been applied and secured to the treatment site, medical device 110 may be removed from the patient's body.

The positioning and deployment of patch 200 (e.g., via movable body 122 of handle assembly 120, and/or by pull wire 118) may be straightforward and user-friendly, which may allow the user to be a surgical technician, while the physician performs one or more other tasks during the procedure. Furthermore, as discussed above, because expandable structure 210 may be maintained in a retracted state against end cap 130, patch 200 does not need to be delivered to the treatment site via working channel 143 of endoscope 140, as it is already positioned on distal end 131 of end cap 130. Accordingly, patch 200 may have a larger size than other mesh patches used to treat ulcers since there is no risk that patch 200 will become stuck within, or otherwise impair, working channel 143. Therefore, larger treatment sites may be treated using patch 200.

Additionally, the capability of patch 200 to be positioned and repositioned provides flexibility during treatment of a patient. For example, if a physician or other operator does not position patch 200 directly over the treatment site, he or she has the capability to simply reposition patch 200 prior to deployment of patch 200. Moreover, patch 200 may be positioned and repositioned either by endoscope 140 or by inner coil 116, which may allow for enhanced precision in positioning patch 200. Finally, as patch 200 may be transparent, or may include a central opening 214, visualization device(s) 142 on distal face 149 of endoscope 140 may remain uninhibited, thereby facilitating visualization of the treatment site by the physician/operator during positioning and repositioning.

While principles of this disclosure are described herein with the reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical device, comprising:

a handle including a main body and a movable body;

a sheath element coupled to the handle;

an actuation element disposed within the sheath element;

an end cap configured to be coupled to a distal end of another medical device;

a patch positioned on the end cap and coupled to the actuation element, the patch comprising:

a mesh, and an expandable structure coupled to the mesh, wherein the expandable structure is configured to be coupled to the actuation element, and wherein the expandable structure is further configured to cause the mesh to retract and expand; and a release mechanism coupled to the expandable structure, wherein the release mechanism is coupled to a pull wire disposed within the actuation element.

2. The medical device of claim 1, wherein the handle comprises a portion configured to decouple the pull wire from the actuation element such that the pull wire moves independently of the actuation element.

3. The medical device of claim 1, wherein the release mechanism comprises a ball and a yoke, wherein the ball is coupled to a distal end of the pull wire, and wherein the ball is configured to fit within a slot disposed in the yoke.

4. The medical device of claim 3, wherein the ball is configured to be detached from the yoke to release the expandable structure from the actuation element.

5. The medical device of claim 1, wherein the expandable structure comprises a star-shaped configuration.

6. The medical device of claim 5, wherein the star-shaped configuration includes at least four pointed segments.

7. The medical device of claim 1, wherein the expandable structure comprises a shape memory material.

8. The medical device of claim 1, wherein the actuation element is configured to move the patch from a first position to a second position.

9. The medical device of claim 8, wherein the patch is positioned on the end cap when the patch is in the first position, and wherein the patch is in a position distal to a distal end of the end cap when the patch is in the second position.

10. The medical device of claim 9, wherein the patch is configured to remain in a retracted configuration when in the first position.

11. The medical device of claim 9, wherein the patch is configured to expand into an expanded configuration when in the second position.

12. The medical device of claim 1, wherein the patch further comprises a central opening.

13. The medical device of claim 1, wherein the patch is at least partially transparent.

14. A medical device, comprising:

a handle disposed at a proximal end of the medical device, the handle including a main body, a movable body, and a decoupling mechanism;

a sheath element;

an actuation element disposed within the sheath element and coupled to the decoupling mechanism;

a pull wire disposed within the actuation element and coupled to the decoupling mechanism;

an end cap configured to be coupled to a distal end of another medical device; and a patch positioned on the end cap, the patch comprising:

a biocompatible mesh, and an expandable structure coupled to the biocompatible mesh; and a release mechanism coupled to each of the expandable structure and the pull wire, wherein the expandable structure is configured to cause the patch to expand.

15. The medical device of claim 14, wherein the release mechanism comprises a yoke portion and a ball portion configured to fit within a slot of the yoke portion, and wherein the ball portion extends from the pull wire.

16. An end cap assembly for a medical device, the end cap assembly comprising:

an end cap body configured to be coupled to a distal end of an endoscope;

a patch positioned on a distal end of the end cap body, the patch comprising:

a mesh, and an expandable structure coupled to the mesh, wherein the expandable structure is configured to transition the patch between a retracted configuration and an expanded configuration, wherein, in the retracted configuration, the expandable structure is disposed adjacent to the end cap body, and wherein, in the expanded configuration, the expandable structure causes the patch to extend radially outward to engage a treatment site; and a release mechanism coupled to the expandable structure, wherein the release mechanism is further configured to receive a pull wire such that proximal movement of the pull wire selectively releases the patch from the end cap body.

17. The end cap assembly of claim 16, wherein the release mechanism comprises a yoke portion coupled to the expandable structure and a ball portion configured to be received within a slot of the yoke portion.

18. The end cap assembly of claim 17, wherein the ball portion is coupled to a distal end of the pull wire, and wherein the ball portion is configured to detach from the slot of the yoke portion to release the patch from the end cap assembly.

19. The end cap assembly of claim 16, wherein the end cap body further comprises an end cap ring extending radially outward from the end cap body between a proximal portion and the distal end of the end cap body.

20. The end cap assembly of claim 19, wherein the end cap ring includes at least one through-hole configured to receive a coil element, and wherein the coil element is configured to receive the pull wire such that the proximal movement of the pull wire within the coil element selectively releases the patch from the end cap assembly.

* * * * *